United States Patent [19]

Heaven et al.

[11] Patent Number: 5,524,633
[45] Date of Patent: Jun. 11, 1996

[54] SELF-DEPLOYING ISOLATION BAG

[75] Inventors: Malcolm D. Heaven, Hopewell, N.J.; Robert L. Hess, Portola Valley, Calif.; Ary S. Chernomorsky, Plainsboro, N.J.

[73] Assignee: Advanced Surgical, Inc., Princeton, N.J.

[21] Appl. No.: 130,503

[22] Filed: Oct. 1, 1993

Related U.S. Application Data

[63] Continuation-in-part of Ser. No. 797,727, Nov. 25, 1991, Pat. No. 5,308,327.

[51] Int. Cl.$^6$ ............................................ A61B 10/00
[52] U.S. Cl. ........................... 128/749; 128/DIG. 24; 600/37; 606/114
[58] Field of Search ............................ 604/327–328, 604/356; 606/114, 127, 128, 139, 151; 128/749, DIG. 24; 600/37

[56] References Cited

U.S. PATENT DOCUMENTS

| | | |
|---|---|---|
| 6,796 | 10/1949 | Haile . |
| 157,343 | 12/1974 | Molesworth . |
| 318,535 | 5/1985 | Bihler . |
| 734,498 | 7/1903 | Bachler . |
| 901,376 | 10/1908 | Roberts . |
| 923,303 | 6/1909 | Shults . |
| 1,213,005 | 1/1917 | Pillsbury . |
| 1,970,802 | 8/1934 | Johnson . |
| 2,032,859 | 3/1936 | Wappler . |
| 2,570,921 | 10/1951 | Collins . |
| 2,667,437 | 1/1954 | Zoubek . |
| 2,798,523 | 7/1957 | Barrett . |
| 2,847,997 | 8/1958 | Tibone . |
| 2,927,584 | 3/1960 | Wallace . |
| 3,048,514 | 8/1962 | Bentele et al. . |
| 3,126,307 | 3/1964 | Drittenbass . |
| 3,232,810 | 2/1966 | Reesen . |
| 3,417,745 | 12/1968 | Sheldon . |
| 3,483,859 | 12/1969 | Pittman . |
| 3,509,883 | 5/1970 | Dibelius . |
| 3,605,747 | 9/1971 | Pashkow . |
| 3,712,772 | 1/1973 | Hunkar . |
| 3,782,370 | 1/1974 | McDonald . |
| 3,834,394 | 9/1974 | Hunter et al. . |
| 3,841,304 | 10/1974 | Jones . |
| 3,841,317 | 10/1974 | Awais . |
| 3,863,639 | 2/1975 | Kleaveland . |

(List continued on next page.)

FOREIGN PATENT DOCUMENTS

| | | |
|---|---|---|
| 490714A1 | 6/1992 | European Pat. Off. . |
| 2514428A | 10/1976 | Germany . |
| 131620 | 7/1978 | Germany . |

*Primary Examiner*—Corrine M. McDermott
*Attorney, Agent, or Firm*—Burns, Doane, Swecker & Mathis

[57] ABSTRACT

An expandable and collapsible isolation bag having at least two layers which are bonded together at a plurality of connection sites distributed over a surface of the bag and a system for supplying a fluid between the two layers and opening the isolation bag. The two layers preferably include polyurethane film and the bag may further include a lubricous outer surface, such as a nylon mesh layer, bonded to the polyurethane film. A neck channel may be formed around the openable end of the isolation bag for supporting a drawstring which is movable through the neck channel to close the open end of the bag. The bag can be made by bonding the nylon mesh layer to two layers of polyurethane film using a radio frequency welder to form a plurality of weld sites distributed across the surface of the laminate. The drawstring is then introduced into the neck channel. The finished laminate with the drawstring is welded to form a bag assembly having an opening at one end. A neck portion of the bag assembly is then connected to a bag coupling on the end of the hollow rod. A compressive band of heat-shrinkable material may be used to secure the bag assembly on the rod. A handle assembly is bonded to the rod and the drawstring is threaded through a slidable seal between the rod and an injection tube. The end of the drawstring is connected to a movable portion of the handle or to a pulling ring.

13 Claims, 6 Drawing Sheets

U.S. PATENT DOCUMENTS

| | | |
|---|---|---|
| 4,076,872 | 2/1978 | Lewicki et al. . |
| 4,172,301 | 10/1979 | Everard et al. . |
| 4,174,715 | 11/1979 | Hasson . |
| 4,190,042 | 2/1980 | Sinnreich . |
| 4,198,981 | 4/1980 | Sinnreich . |
| 4,240,433 | 12/1980 | Bordow et al. . |
| 4,268,338 | 5/1981 | Peterson . |
| 4,311,146 | 1/1982 | Wonder . |
| 4,312,353 | 1/1982 | Shahbabian . |
| 4,393,872 | 7/1983 | Reznik . |
| 4,428,375 | 1/1984 | Ellman . |
| 4,557,255 | 12/1985 | Goodman . |
| 4,611,594 | 9/1986 | Grayhack . |
| 4,654,028 | 3/1987 | Suma . |
| 4,735,603 | 4/1988 | Goodson et al. . |
| 4,739,762 | 4/1988 | Palmaz . |
| 4,744,363 | 5/1988 | Hasson . |
| 4,796,629 | 1/1989 | Grayzel . |
| 4,802,479 | 2/1989 | Haber et al. . |
| 4,803,029 | 2/1989 | Iversen et al. . |
| 4,857,129 | 8/1989 | Jensen et al. . |
| 4,873,978 | 10/1989 | Ginsburg . |
| 4,875,482 | 10/1989 | Hariri . |
| 4,899,747 | 2/1990 | Garren et al. . |
| 4,909,789 | 3/1990 | Taguchi et al. . |
| 4,957,477 | 9/1990 | Lundback . |
| 4,984,564 | 1/1991 | Yuen . |
| 4,999,074 | 3/1991 | Afeyan . |
| 5,027,793 | 7/1991 | Englehardt et al. . |
| 5,035,232 | 7/1991 | Lutze et al. . |
| 5,037,379 | 8/1991 | Clayman et al. . |
| 5,080,088 | 1/1992 | Le Vahn . |
| 5,143,082 | 9/1992 | Kindberg et al. . |
| 5,163,949 | 11/1992 | Bonutti . |
| 5,176,687 | 1/1993 | Hasson et al. . |
| 5,178,133 | 1/1993 | Pena . |
| 5,195,507 | 3/1993 | Bilweis . |
| 5,234,439 | 8/1993 | Wilk et al. . |
| 5,256,132 | 10/1993 | Snyders ............... 600/16 |
| 5,279,539 | 1/1994 | Bohan et al. ............ 600/37 |
| 5,312,416 | 5/1994 | Spaeth et al. ............ 606/114 |
| 5,337,754 | 8/1994 | Heaven et al. ............ 128/749 |

SELF-DEPLOYING ISOLATION BAG

CROSS-REFERENCE TO RELATED APPLICATION

The present application is a continuation-in-part of U.S. patent application Ser. No. 07/797,727 which was filed on Nov. 25, 1991, now U.S. Pat. No. 5,308,327 the disclosure of which is hereby incorporated by reference.

FIELD OF THE INVENTION

The present invention generally relates to endoscopic surgery, and more particularly, to means and methods for containing body tissue or structures, for example gall bladders, appendix, etc.

BACKGROUND OF THE INVENTION

A major problem associated with minimally invasive endoscopic surgical procedures is that of aseptic removal of diseased or contaminated tissue. For example, during the laparoscopic excision of a gangrenous gallbladder, the infected organ must first be isolated and contained inside the abdominal cavity before it can be safely removed without risking the spread of disease. Therefore, the excised tissue is often contained in what is generally referred to as an isolation bag, inside the body cavity, prior to and during removal.

Currently available isolation bags are difficult to use and manufacture. For example, U.S. Pat. No. 5,037,379 to Clayman discloses a net which will not prevent the transfer of diseased cells. U.S. Pat. No. 4,557,255 to Goodman discloses a bag which may not deploy conveniently for accepting the organ or tissue. U.S. Pat. No. 5,215,521 to Cocharan discloses a bag with tubes and staves which is also difficult to use and manufacture.

The present invention provides solutions to these and other problems associated with conventional isolation bags.

SUMMARY OF THE INVENTION

The present invention generally relates to a surgical device and a method of making that surgical device. The disclosed device includes an expandable and collapsible isolation bag having at least two layers which are bonded together at a plurality of connection sites to form fluid channels distributed over a surface of said bag. The device preferably includes means for supplying a fluid to the fluid channels to open the isolation bag. The two layers preferably comprise polyurethane films and the bag may further include a nylon mesh layer bonded to the polyurethane film to strengthen and provide lubricity to the bag when the bag is deployed through an ejection tube. A neck channel may be formed around the openable end of the isolation bag for supporting a drawstring which can be pulled to close the open end of the bag.

The fluid supplying means may include a hollow rod which is slidable inside the ejection tube. One end of the hollow rod includes a bag coupling which is inserted between the two polyurethane layers of the bag. A handle assembly including a valve is connected to the other end of the rod. A slidable seal may be provided in the annulus between the ejection tube and the rod. The drawstring is threaded up the annulus between the rod and the ejection tube to the handle assembly where it may be attached to suitable pulling means which can be grasped by the surgeon for closing the bag.

The method of making the surgical device includes bonding a nylon mesh layer with two layers of polyurethane film using a high frequency welder. The welder includes a shaped die which forms a plurality of weld sites distributed across the surface of the laminate and also forms seams and the neck channel at the edges of the laminate. The drawstring is then introduced into the neck channel. The finished laminate with the drawstring is then wrapped around a mandrel and a longitudinal seam formed, after which the bag can be folded and a bottom seam can be welded to form a bag assembly having an opening at one end. A neck portion of the bag assembly is then connected to a bag coupling on the end of the hollow rod. A compressive band of heat-shrinkable material may be used to secure the bag assembly on the rod. The handle assembly is bonded to the rod and the drawstring is threaded through the slidable seal on the rod and a passage in the handle assembly. The end of the drawstring is connected to a movable portion of the handle or other pulling means such as a ring member.

BRIEF DESCRIPTION OF THE DRAWING

The invention will now be described in greater detail, by way of example, with reference to the accompanying drawing in which.

DETAILED DESCRIPTION OF THE PREFERRED EMBODIMENTS

Figure 1:
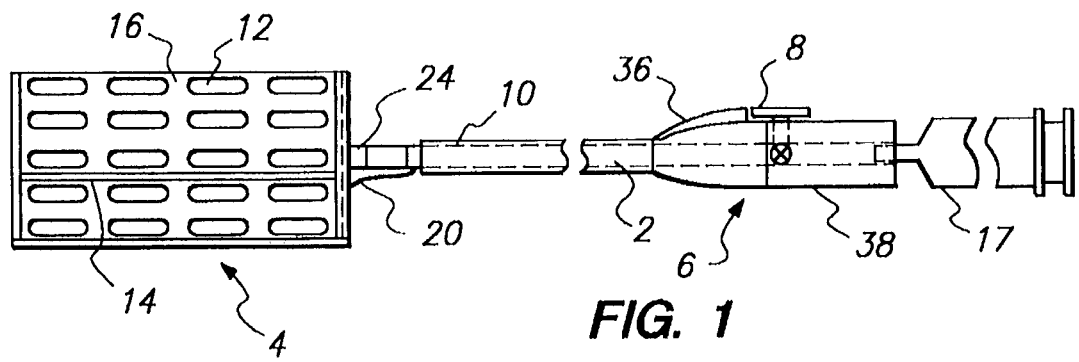
FIG. 1 shows a self-deploying isolation bag device.

The present invention generally relates to a collapsible article which may be deployed and inflated either pneumatically or hydraulically to form a rigid or semi-rigid isolation bag for in-situ retrieval of surgically removed tissue and specimens during minimally invasive surgical procedures such as laparoscopy. In a typical application, the collapsed bag is first stored in a confined space, e.g., a small diameter tubular member (referred to as an ejection tube). The bag may then be inserted into a body cavity, such as the abdominal cavity, through a device known as a trocar. Upon clearing the trocar, the bag is physically ejected from the end of the tubular member and inflated with a suitable medium such as air, water, or saline solution. Upon deployment and pressurization, the bag assumes its preferred shape inside the body cavity and can be used as a container for holding surgically removed tissue. Thus, the bag can be used to safely contain and remove contaminated or diseased tissue, such as a gangrenous gall bladder, from a body cavity.

The inflatable section of the device may be manufactured using numerous forming processes. Methods which may be employed to make the device include, but are not limited to, blow-molding, injection molding, dip molding, welding from sheet or tubing using adhesives, ultrasonic welding or high frequency welding, and other methods that will be apparent to those skilled in the art. In particular it has been found that complex shapes can be manufactured from welded, woven, or sewn fabric using, for example, numerically controlled knitting, welding and/or weaving machines. The fabric may be made pressure or fluid tight by dipping it in, for example, natural rubber latex, or other flexible material such as polyurethane. The fabric structure provides high multi-axial reinforcement, and hence, excellent strength. In addition, various shapes may be made from welded fabric and fabric composites. For example, polyurethane impregnated or laminated polyester or nylon fabrics can be welded to form coherent structures using techniques apparent to those skilled in the art. Welded structures of polyurethane or latex laminated to polyester or nylon cloth in which the laminating or coating polymer does not fully penetrate the weave have been found appropriate for preserving a desirable lubricous nature, or feel, of the cloth on the outer surface of the bag.

Other methods of providing suitable shapes to the inflated medical devices of the invention will be apparent to those skilled in the art. Additional shapes may be obtained by using a preforming operation, such as vacuum forming, prior to welding sheets together. In certain cases it may be advantageous to form the basic shape of the structure and then turn the article inside out so that any external seams will reside on the inside surface of the article, yielding a less traumatic surface on the exterior.

The inflatable isolation bag represents a considerable improvement over existing devices. The isolation bag has a structure which can be deployed and held open by the application of slight pneumatic or hydraulic pressure in a series of interconnecting passages contained within a wall of the bag. These channels may run longitudinally along the length of the body of the bag, or circumferentially around the body of the bag, or a combination of these and other angles. They may cover the entire bag surface, or only part of the surface. For example, the channels may extend only 50% of the length of the bag. The bag wall can include additional elements, such as ribs or wires of springy material as defined herein that will assist the bag in opening and maintaining its shape with or without pneumatic or hydraulic pressure.

By way of example, according to a preferred embodiment the bag can be manufactured from polyurethane films. These films can be welded together using any suitable method, as will be apparent to those skilled in the art. In addition, the structure can be blow-molded, bonded, or formed using any suitable process, then irradiated to cross-link the polymer, heated above its crystalline melting point, distorted in a melted condition to a bag shape using a plunger or by blow molding the shape using high pressure air, and finally cooled below its crystalline melting point to impart structural stability.

The open end of the bag can include a flexible member or members to aid in deployment of the bag. For instance, a "springy" material, such as a shape memory alloy, fiber reinforced plastics, engineering plastics, and other materials known to those skilled in the art that have sufficient flexibility and yield strength such that they do not permanently deform during storage can be incorporated in the bag. The flexible member should have sufficient strength to bias the neck of the bag in an open configuration that is still easily collapsible. Also, a hypotube of springy material as defined above which incorporates, for example, laser drilled holes near the distal end could be used as a combined flexible member and inflation member.

Alternatively, the device may be constructed without the flexible member and instead the bag can be opened solely by supplying fluid to the fluid channels. A drawstring closure mechanism permits the neck to be drawn closed after tissue has been placed therein.

The device can be folded and inserted into a containment or ejection tube. The dimensions of the tube are suitable for insertion into, for example, the abdominal cavity using a trocar. Upon exiting the trocar, the device is ejected manually from its tube whereupon, for example, a wire of springy material in the neck region may help deploy the neck opening. However, as noted above, the device may be used without the wire in the neck region and the neck may simply be urged open by supplying fluid to the fluid channels in the wall of the bag. Upon inflation, these channels force the isolation bag to take a preferred orientation, and allow the surgeon easy access for inserting the diseased tissue or organ. The channels in the bag are then aspirated, allowing the bag to collapse. The bag can be closed by pulling the top of it into the ejection tube. If the device includes a drawstring closure, the drawstring in the neck region is drawn tight, thus closing the bag.

The inner rim of the neck may be coated with a high tack polymer coating such as, for example, silicone gel to further ensure that there is no leakage when the bag is closed. The bag can now be taken into the neck of the trocar and if not too full, it may be fully withdrawn. In cases where the organ is too large to fit in the trocar, the bag may be worked out through the wound left in the skin by the trocar after its removal, or a morcellator may be introduced into the neck of the bag upon its exit from the wound and the tissue reduced in size prior to withdrawal of the bag from the body cavity.

In yet another embodiment, the bag is made more readily manipulatable by virtue of short spring elements in the neck area. In addition to these assisting with making the bag more maneuverable, they also assist with opening the neck of the bag. Additionally, the bag can contain a means of articulation, such that the angle of the bag can be changed to assist the surgeon with alignment toward the specimen it is intended to capture. For example, if a bag which has an angle of repose at right angles to the ejection tube is difficult to withdraw into the tube, it may be desirable to angle the bag at a suitable angle such as 60° to the ejection tube to facilitate withdrawal of the bag back into the tube. It may also be advantageous in some procedures to have the isolation bag be detachable from its ejection tube. The detached bag could then be removed from the body cavity at a later time.

A further embodiment of this device pertains to cases wherein very high strength is needed in the bag. In this instance, it is proposed that the bag be, for example, constructed of a fiber or cloth reinforced polymer. Among suitable materials there may be mentioned, but are not limited to, polyurethane, polyester fabric or nylon fabric composites, natural rubber polyester fabric or nylon fabric composites, fabrics such as Goretex®, and composites and laminates of suitable materials, as will be apparent to those skilled in the art. In particular it may be mentioned that welded laminates of polyurethane and nylon fabric or polyethylene terephthalate fabric, where the fabric surface is on the outside of the bag, offer excellent re-entry performance due to the surface characteristics of the fabric. The bag may also be coated with surface treatments, such as hydrophilic polymers, to aid removal through the wound.

In the case of reinforced materials, an alternative manufacturing process must be used, due to the inextensibility of the material. One such method would be to sew or weld the article to the required shape, incorporating such ribs and channels as may be necessary. The stitching site may then be sealed with a suitable polymer, e.g., natural rubber latex. Another method is to weld the structure using, for example, high frequency welding. Other methods will be apparent to those skilled in the art.

Various aspects of the invention will now be described with reference to FIGS. 1–16.

FIG. 1 shows a self-deploying isolation bag device in a fully extended position. The device includes an internal plunger or hollow rod 2 (see FIG. 2) having a bag assembly 4 at one end and a handle assembly 6 at the other end of the rod 2. A conventional stop-cock valve 8 is connected to the end of the hollow rod 2 near the handle assembly 6. The valve 8 allows fluid to be passed through the tube 2 for inflation of the bag and after the bag is inflated the valve 8 can be closed to maintain the bag in the inflated or expanded condition. The rod 2 slides freely inside a delivery or ejection tube 10.

The bag assembly 4 can be formed from a layer of nylon mesh bonded to at least two layers of polyurethane film as described in more detail below with reference to FIGS. 4–11. The nylon mesh and polyurethane layers are bonded together at weld sites 12 and seams 14 which form air or fluid channels are formed between the two polyurethane layers. A fluid such as air, water, or saline solution is supplied to the fluid channels by a syringe 17. The syringe 17 may be replaced or augmented by any suitable source of fluid pressure, such as a pump, compressor, or squeeze bulb.

Figure 5:
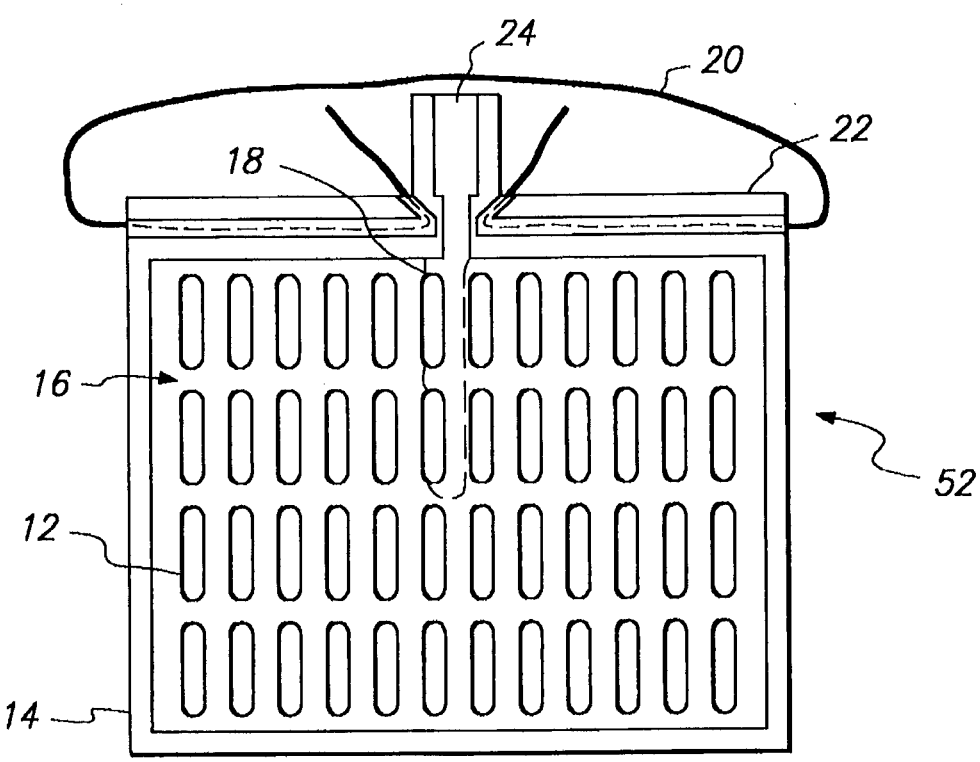

One or more optional ribs 18 may also extend through the bag assembly 4 for providing shape and rigidity to the bag assembly 4, as shown in FIG. 5. For example, a suitably flexible plastic rib 18 may be secured to the tip of rod 2 and extend along the length of the bag assembly 4 between the nylon mesh and polyurethane layers. The rib 18 may also be arranged between the two polyurethane layers or omitted entirely.

The bag assembly 4 includes an access opening and a purse-string type closure at its open end near the tip of the rod 2. A drawstring 20 of Kevlar thread or other suitable material is threaded through a neck channel or string passage 22 in the bag assembly 4 with one or both ends of the drawstring passing out the handle 6. However, other filament materials such as wire may also be used. The neck channel 22 is preferably formed between the two polyurethane layers by welding the layers along two parallel and spaced-apart weld lines. The drawstring 20 may be looped twice around the circumference of the bag opening inside the neck channel 22 in order to provide a tighter seal when the drawstring is pulled to close the bag. Alternatively, one end of the drawstring can be fixedly held in the layers of the bag and the other end passed through the neck channel and a slip knot whereby a single end of the drawstring can be used to close the bag.

The bag assembly 4 includes a neck portion 24 for securing the bag assembly 4 to the tip of the rod 2 and for passing fluid to the fluid channels. The tip of the rod 2 may be fitted with a bag coupling 26 (see FIG. 2) having a reduced diameter portion 28 at its tip. The portion 28 of the bag coupling 26 fits inside the neck portion 24 of bag assembly 4, preferably between the two polyurethane sheets. The neck portion 24 is then sealed to the bag coupling 26 using a compressive band 30 of heat-shrink material or other sealing means, such as adhesive. A slidable seal 32 provides a fluid tight seal between the rod 2 and the ejection tube 10. Additional slidable seals may also be arranged along the rod 2. A tube cap 34 (see FIG. 3) and/or O-ring may be provided at the top of the ejection tube 10.

The handle assembly 6 may include a stationary portion 36 and a movable portion 38. One or both ends of the drawstring 20 can extend through the annulus between rod 2 and tube 10 and then through a drawstring passage 40 in the stationary portion 36 of the handle assembly 6. The end(s) of the drawstring 20 may be attached to the movable portion 38 of the handle assembly used for pulling the drawstring and closing the bag. The movable portion 38 may take the form of a C-shaped member which fits around the valve 8 and is slidably held on pins 42 extending from stationary portion 36 on each side of the valve 8. Alternatively, the movable portion 38 may take the form of a ring 44 (see FIG. 3), or other shape which is easily gripped and/or which is not attached to the stationary portion 36.

Prior to deployment of the bag, the bag assembly 4 is folded tightly and slidably fitted inside the ejection tube 10. The ejection tube 10 is introduced into a delivery device such as a trocar until the tip of the ejection tube 10 is inside a body cavity. The rod 2 is pushed through the ejection tube 10 until the bag assembly 4 is ejected inside the body cavity. The valve 8 is opened and a pressurized fluid, such as air is forced down the inside of rod 2 and into the air channels 16 in the bag assembly 4. Once the bag assembly 4 is inflated inside the body cavity, the valve 8 may be closed to maintain pressure in the fluid channels 16. Tissue, such as gangrenous gall bladder tissue, may then be placed inside the open bag assembly 4.

Figure 3:
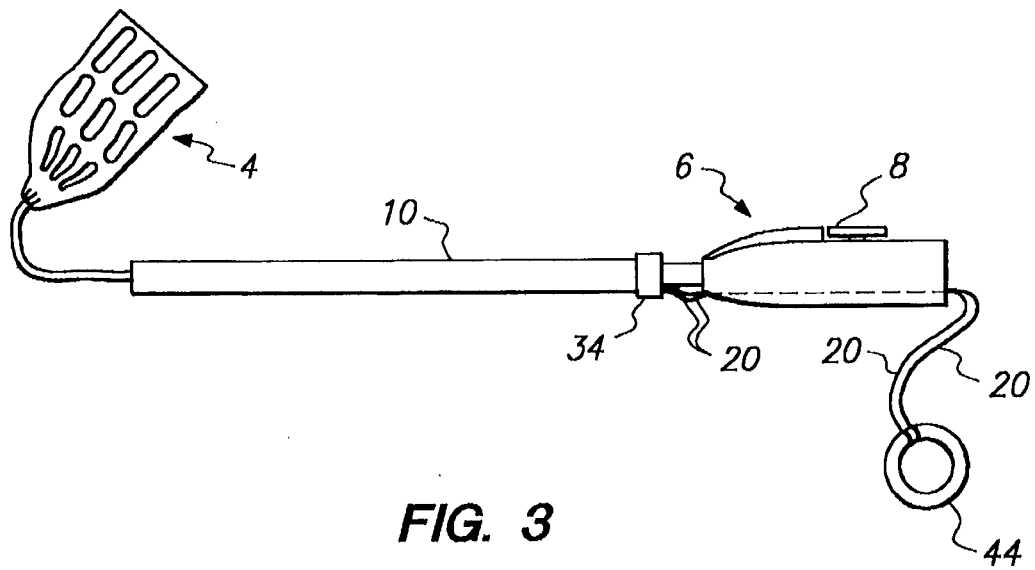
FIG. 3 illustrates an alternative handle assembly that may be used with the device of FIG. 1.

The bag assembly 4 is then aspirated and closed by pulling on the movable portion 38 of handle assembly 6 in order to tension drawstring 20. Once the open end of the bag assembly 4 is closed, the device may be removed from the body cavity. Alternatively, the closed bag assembly 4 may be separated from the rod 2 inside the body cavity as illustrated in FIG. 3. For example, the portion of the bag assembly 4 above the drawstring closure may be cut to separate the bag assembly 4 from the rod 2 or the bag assembly 4 may simply be torn off the rod 2 by firmly withdrawing the rod 2 while using the ejection tube 10 to hold the bag assembly 4 in the body cavity until the neck portion 24 pulls apart.

Alternatively, the handle can be made resposable by providing coupling 26 with a releasable connection for detaching the bag assembly from the rod. This feature allows an alternative method of manufacture in which the bag assembly contained within a short ejection tube extension may be attached to a reusable handle. The drawstring end(s) are attached to a pulling means incorporated in the reusable handle. This allows cost reductions to be realized by hospitals in that only the bag and ejection tube extension are disposable.

Figure 2:
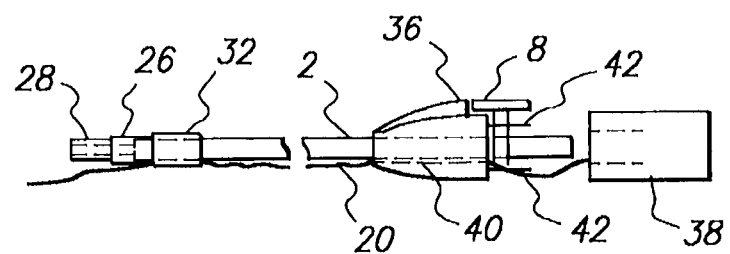
FIG. 2 shows internal features of the device in FIG. 1.
Figure 4:
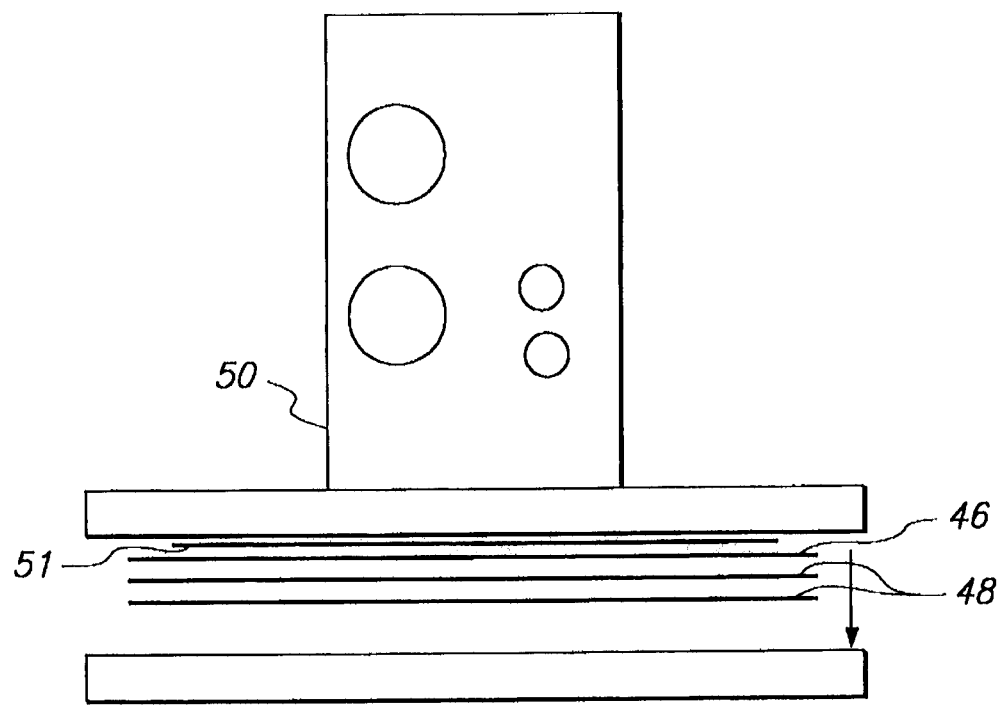
FIGS. 4 through 11 illustrate various steps for making the device shown in FIG. 1.

FIGS. 4–11 schematically illustrate various consecutive steps for making the device in FIGS. 1–3. FIG. 4 shows a nylon mesh layer 46 being bonded to two polyurethane film layers 48 when the layers 48 are bonded together by a radio frequency welder 50 to form a laminate 52. That is, the polyurethane melts and fills the interstices in the nylon mesh to form the laminate 52. The welder 50 includes a shaped die 51 for forming the weld sites 12, seams 14, and fluid channels 16.

Figure 6:
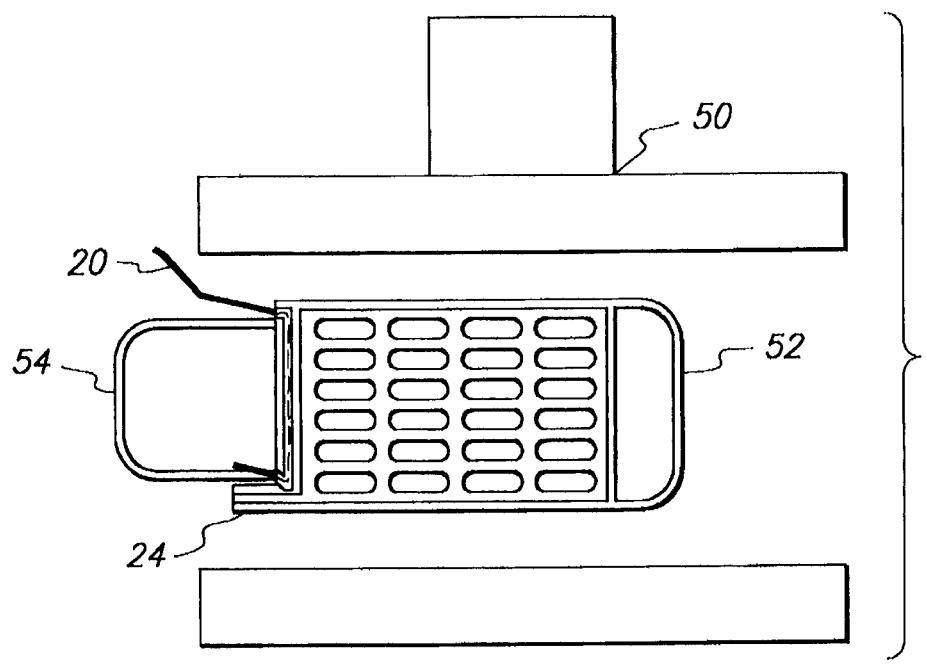
Figure 7:
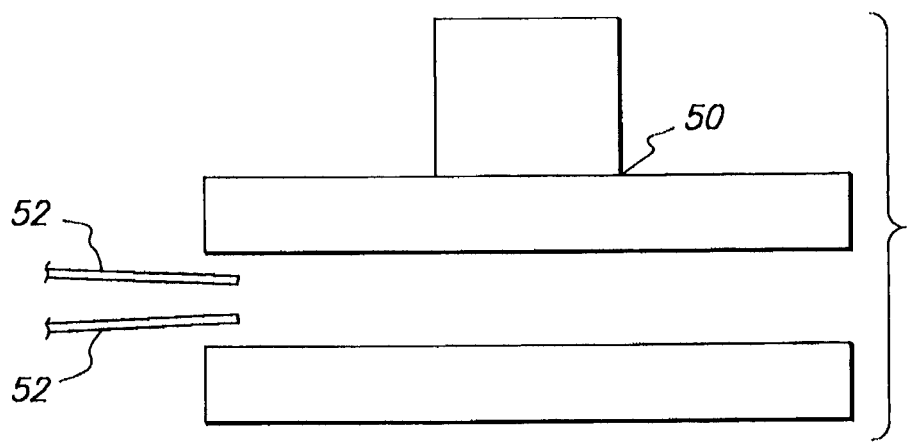

FIG. 5 shows drawstring 20 being introduced into the neck channel 22 in the laminate 52 with a suitable weld pattern wherein outer edges of the laminate are welded together except at the neck portion 24. The weld sites 12 in FIG. 5 are distributed uniformly over the entire laminate and each weld site has an oblong or oval shape. However, other weld shapes and patterns may also be used. FIG. 6 shows the finished laminate 52 with overlapping side edges placed over a mandrel 54 and beneath the welder 50 for producing a cylindrical shape by welding along the overlapped side edges of the laminate. The bottom of the bag assembly can be closed by welding a separate piece to the bottom edge of the laminate or the laminate can be flattened and opposed bottom edges of the laminate can be welded together to form the bottom of the bag, as shown in FIG. 7.

Figure 8:
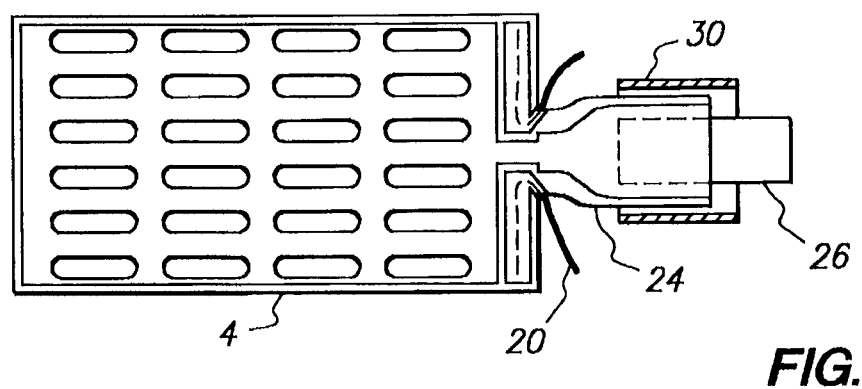
Figure 9:
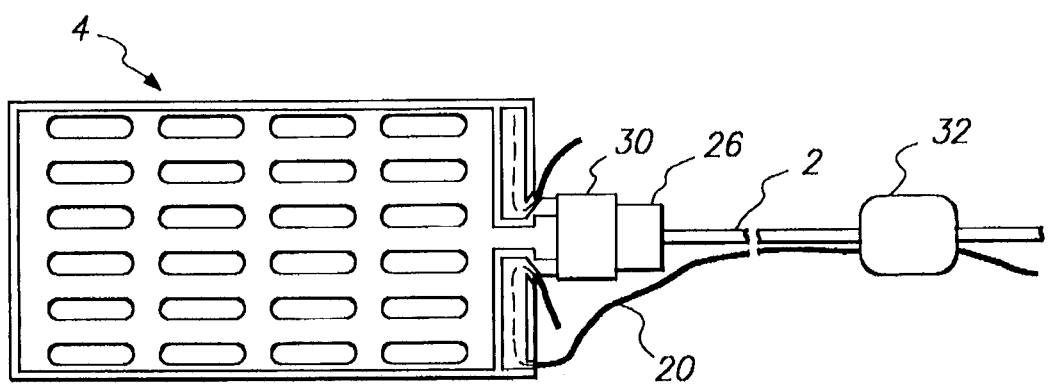
Figure 10:
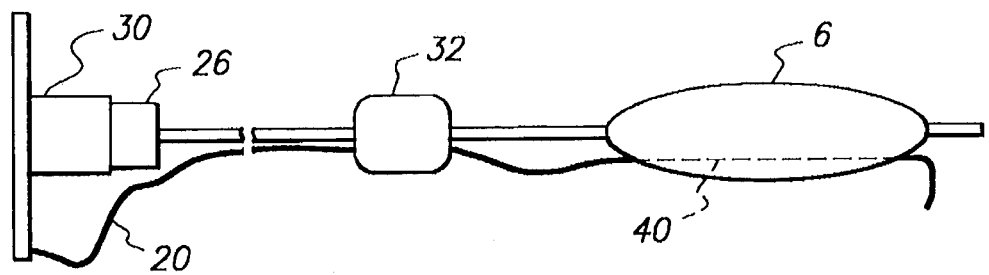
Figure 11:
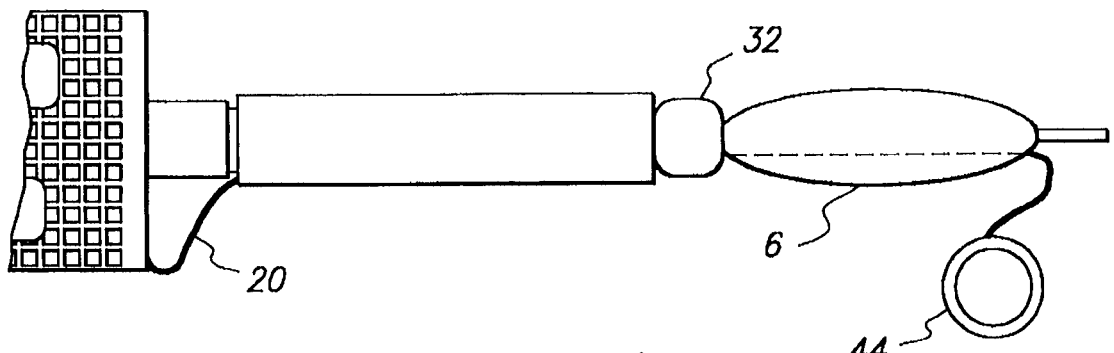

FIG. 8 illustrates the compressive band 30 being fitted on the neck portion 24 of the bag assembly 4 and the bag coupling 26 on the rod 2. The compressive band 30 is preferably a tube of conventional heat-shrinkable plastic material. In FIG. 9, the drawstring 20 is threaded through the seal 32 which may also take the form of an elastomeric O-ring. In FIG. 10, the handle assembly 6 bonded to the rod 2 includes a drawstring passage 40 through which the drawstring 20 is threaded and pull ring 44 is attached to the drawstring 20.

Figure 12:
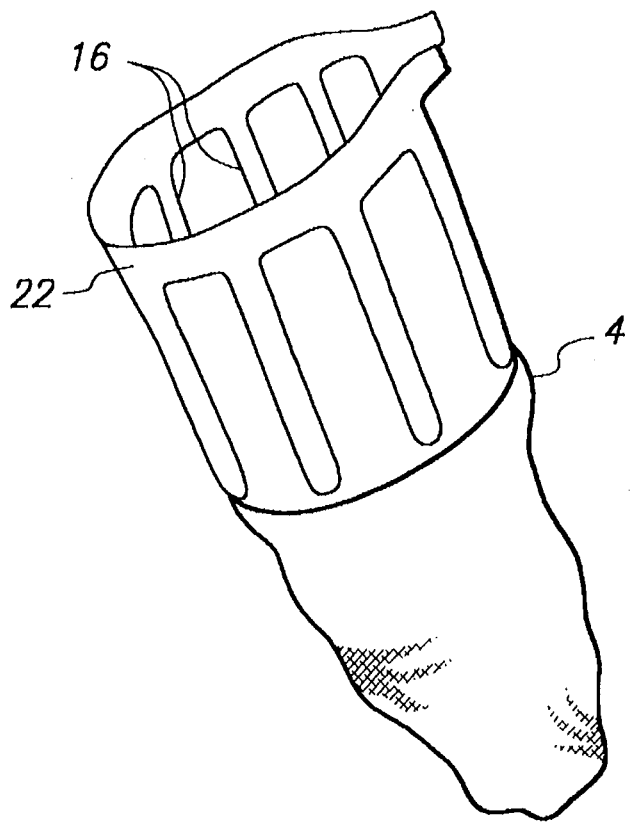
FIGS. 12 through 16 show various other embodiments of a self-deploying isolation bag device.
Figure 13:
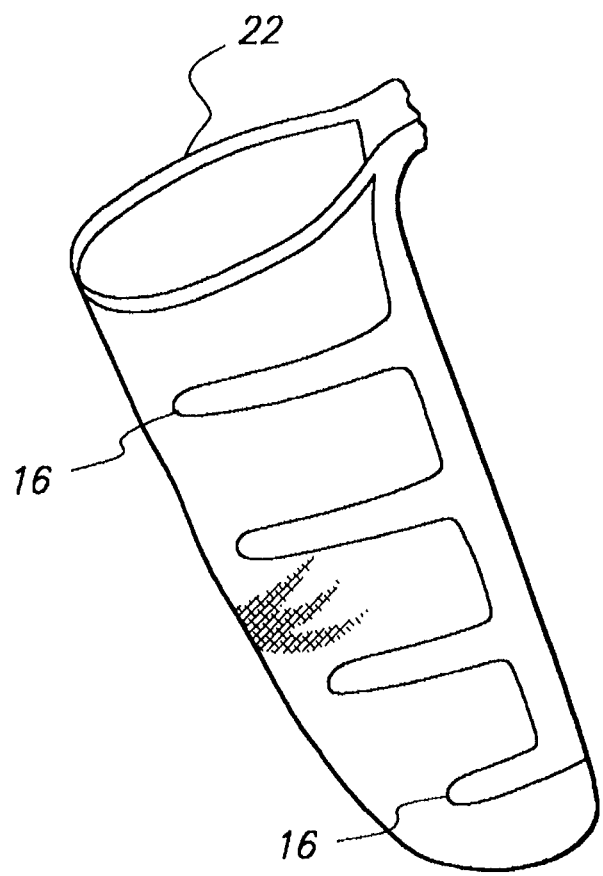

FIGS. 12–16 show isolation bag assemblies 4 having a variety of configurations. In FIG. 12, the fluid channels 16 extend longitudinally along the length of the body of the bag assembly 4. In FIG. 13, the fluid channels 16 extend circumferentially around the body of the bag assembly 4. Although only longitudinal and circumferential arrangements of the fluid channels 16 are shown in the figures, other angled arrangements of the fluid channels or combinations of longitudinal, circumferential, and angled arrangements may also be used. The fluid channels 16 may cover the entire surface of the bag assembly 4, or extend along only a portion of the isolation bag assembly 4.

As shown in FIG. 12, the bag assembly 4 may be formed so as to have the neck channel 22 connected to fluid channels 16. Also, the bottom portion of the bag assembly 4 may be formed from a different material than the top portion. For example, only the bottom portion of the bag assembly 4, may include a coated or composite fabric material, such as nylon, in order to facilitate withdrawal of the bag through the ejection tube. Connecting the neck channel 22 to the fluid channels 16 helps ensure that the neck of the bag is automatically opened and rounded upon pressurization. The neck channel 22 may also include a highly elastic member such as a NiTi shape memory alloy tube for urging the neck open.

Figure 14:
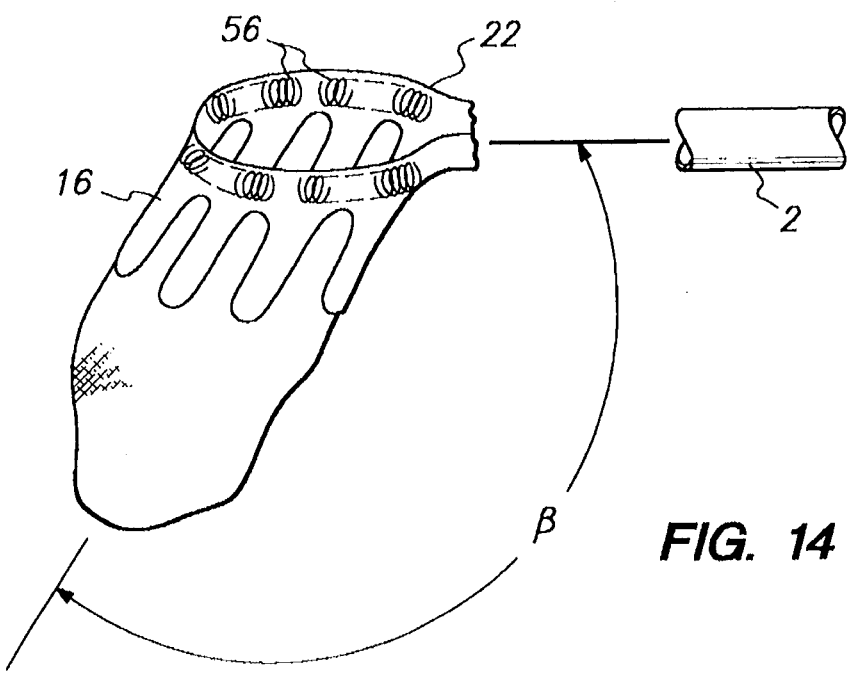
Figure 15:
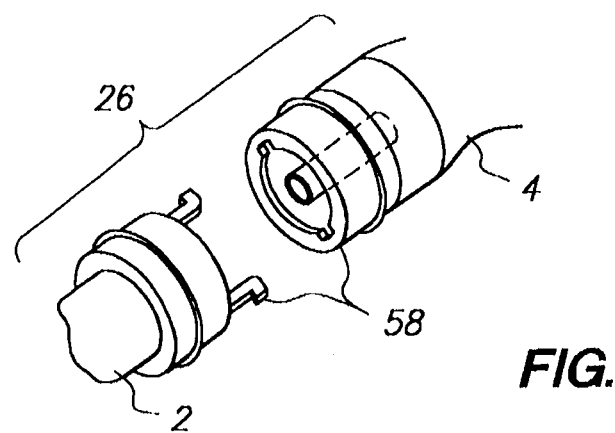

As illustrated in FIG. 14, the bag assembly 4 may also include spring elements 56 in the neck area or on the body of the bag assembly 4. The spring elements 56 may take the form of curved ribs or coil springs arranged in periodic intervals around neck channel 22. The longitudinal axis of the bag assembly 4 can also be formed at an angle β with respect to the longitudinal axis of the rod 2. The angle β may range from 135°–150°, preferably about 150°, to help prevent the bag from catching on the end of ejection tube 10 as it is retracted into the tube 10. As illustrated in FIG. 15, the bag coupling 26 may include a releasable connection 58 which allows the bag assembly to be separated from the rod 2 and the bag assembly can be temporarily left in a patient.

Figure 16:
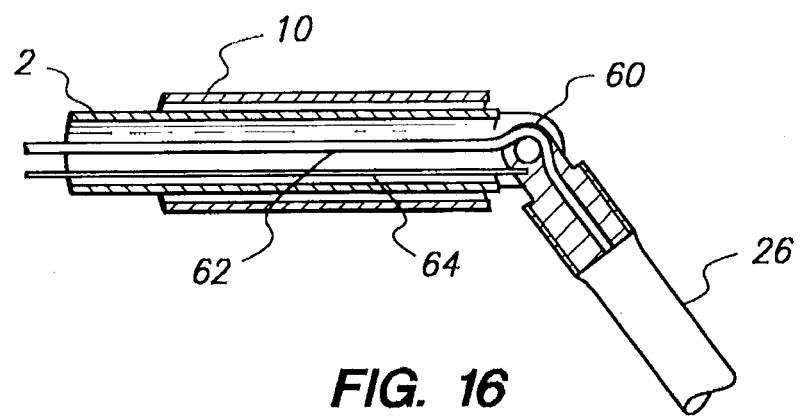

As shown in FIG. 16, the device may also include an articulatable joint 60 for angling the bag assembly 4 with respect to the rod 2. In this case, the rod 2 can comprise a tube fitted within ejection tube 10 and a pivot pin can be used to rotatably support one end of the coupling 26 to the rod 2. Fluid can be supplied to the bag assembly by means of a flexible tube 62 and a wire 64 can be used to pivot the coupling 26 about the pivot pin.

The principles, preferred embodiments, and modes of operation of the present invention have been described in the foregoing specification. However, the invention should not be construed as limited to the particular embodiments which have been described above. Instead, the embodiments described here should be regarded as illustrative rater than restrictive. Variations and changes may be made by others without departing from the scope of the invention as defined by the following claims.

What is claimed is:

1. A surgical device, comprising:
   an expandable and collapsible isolation bag for isolating body tissue, the bag including an access opening which can be opened and closed and at least two layers which are bonded together at a plurality of connection sites distributed over a surface of said bag and forming a plurality of fluid channels between the two layers;
   means for supplying a fluid to the fluid channels for opening the access opening of said isolation bag inside a body cavity; and
   severing means comprising a portion of the isolation bag for detaching part of the isolation bag from the remainder of the isolation bag.

2. The device of claim 1, wherein said at least two layers include polyurethane film.

3. The device of claim 1, wherein said isolation bag further includes a nylon mesh outer surface layer bonded to said at least two layers.

4. The device of claim 1, wherein the isolation bag includes at least one rib disposed between said layers for reinforcing said isolation bag.

5. The device of claim 1, wherein said fluid supplying means includes a hollow rod connected to said isolation bag.

6. The device of claim 5, further comprising an ejection tube surrounding said rod, said rod being slidable within said ejection tube.

7. A surgical device, comprising:
   an expandable and collapsible isolation bag for isolating body tissue, the bag including an access opening which can be opened and closed and at least two layers which are bonded together at a plurality of connection sites distributed over a surface of said bag and forming a plurality of fluid channels between the two layers; and
   means comprising a hollow rod for supplying a fluid to the fluid channels for opening the access opening of said isolation bag inside a body cavity, said hollow rod being connected to said isolation bag, a bag coupling connecting the isolation bag to one end of said rod, a handle assembly with a valve supported at another end of said rod, and an interior of the hollow rod defining a fluid passage which can be opened and closed by the valve.

8. A surgical device, comprising:
   an expandable and collapsible isolation bag for isolating body tissue, the bag including an access opening which can be opened and closed and at least two layers which are bonded together at a plurality of connection sites distributed over a surface of said bag and forming a plurality of fluid channels between the two layers;
   means comprising a hollow rod for supplying a fluid to the fluid channels for opening the access opening of said isolation bag inside a body cavity, said hollow rod being connected to said isolation bag; and
   detachable connecting means for detachably connecting the isolation bag to the rod.

9. A surgical device, comprising:
   an expandable and collapsible isolation bag for isolating body tissue, the bag including an access opening which can be opened and closed and at least two layers which are bonded together at a plurality of connection sites distributed over a surface of said bag and forming a plurality of fluid channels between the two layers;

means comprising a hollow rod for supplying a fluid to the fluid channels for opening the access opening of said isolation bag inside a body cavity, said hollow rod being connected to said isolation bag;

an ejection tube surrounding said rod, said rod being slidable within said ejection tube; and pivot means disposed at one end of said rod to articulate said isolation bag beyond the distal end of the ejection tube.

10. A surgical device, comprising:

an expandable and collapsible isolation bag for isolating body tissue, the bag including an access opening which can be opened and closed and at least two layers which are bonded together at a plurality of connection sites distributed over a surface of said bag and forming a plurality of fluid channels between the two layers;

means for supplying a fluid to the fluid channels for opening the access opening of said isolation bag inside a body cavity; and a coupling and a hollow rod, the isolation bag including a neck portion and the coupling being located between the two layers in the neck portion of the isolation bag, the coupling having a channel therethrough in fluid communication with the fluid channels, the hollow rod being attached to the coupling with the channel in the coupling in fluid communication with an interior of the hollow rod whereby fluid passing through the rod can inflate the isolation bag.

11. A surgical device, comprising:

an expandable and collapsible isolation bag for isolating body tissue, the bag including an access opening which can be opened and closed and at least two layers which are bonded together at a plurality of connection sites distributed over a surface of said bag and forming a plurality of fluid channels between the two layers; and means for supplying a fluid to the fluid channels for opening the access opening of said isolation bag inside a body cavity, the isolation bag including severing means at the access opening of the isolation bag, the severing means comprising a neck portion of the isolation bag which can be separated from the remainder of the isolation bag by pulling the neck portion until it ruptures.

12. A surgical device, comprising:

an expandable and collapsible isolation bag for isolating body tissue, the bag including an access opening which can be opened and closed and at least two layers which are bonded together at a plurality of connection sites distributed over a surface of said bag and forming a plurality of fluid channels between the two layers;

means for supplying a fluid to the fluid channels for opening the access opening of said isolation bag inside a body cavity, said isolation bag including a neck channel extending around the access opening of said isolation bag and a drawstring located in the neck channel;

pulling means attached to the drawstring for pulling the drawstring and closing the open end of the isolation bag;

the means for supplying a fluid including a hollow rod in fluid communication with the fluid channels and a handle at one end of the hollow rod, at least one end of the drawstring passing through said handle.

13. The device of claim 12, wherein the at least one end of the drawstring is attached to said pulling means for pulling the drawstring and closing the access opening of the isolation bag.

* * * * *